United States Patent [19]
Nagel

[11] Patent Number: 6,155,823
[45] Date of Patent: Dec. 5, 2000

[54] SNAP-ON LIGHT SHIELD FOR A DENTAL COMPOSITE LIGHT CURING GUN

[75] Inventor: Rich Nagel, West Chicago, Ill.

[73] Assignee: Bisco Inc., Schaumburg, Ill.

[21] Appl. No.: 09/336,232

[22] Filed: Jun. 18, 1999

[51] Int. Cl.$^7$ .................................................. A61C 1/00
[52] U.S. Cl. ........................... 433/29; 433/229; 359/361; 250/515.1
[58] Field of Search ............................. 433/29, 116, 229; 250/515.1; 359/361, 889, 892

[56] References Cited

U.S. PATENT DOCUMENTS

| | | | |
|---|---|---|---|
| 4,522,594 | 6/1985 | Stark et al. | 433/229 |
| 4,611,992 | 9/1986 | Lokken | 433/29 |
| 4,737,104 | 4/1988 | Croll | 433/229 |
| 5,275,559 | 1/1994 | Ribel | 433/116 |
| 5,288,231 | 2/1994 | Kuehn et al. | 433/29 |
| 5,509,800 | 4/1996 | Cunningham et al. | 433/29 |
| 5,749,724 | 5/1998 | Cheng | 433/29 |
| 5,759,032 | 6/1998 | Bartel | 433/29 |

FOREIGN PATENT DOCUMENTS

0750889A1  1/1997  European Pat. Off. .

*Primary Examiner*—Todd E. Manahan
*Attorney, Agent, or Firm*—Marshall, O'Toole, Gerstein, Murray & Borun

[57] ABSTRACT

A light shield for a dental composite curing gun which can be easily snapped on and off of a probe of the gun is provided. The shield includes a tinted, transparent main body which absorbs certain components of light reflected from a tooth surface being restored, thereby enabling the operator to have a complete field of vision, while protecting the operator from harmful and distracting reflections. The snap-on attachment mechanism includes first and second deformable legs having a receiving notch formed therebetween, such that the shield can be pushed on to and pulled from the probe by deforming the legs. The entire shield and snap-on connection mechanism are manufactured from a unitary piece of material which can be completely sterilized.

20 Claims, 3 Drawing Sheets

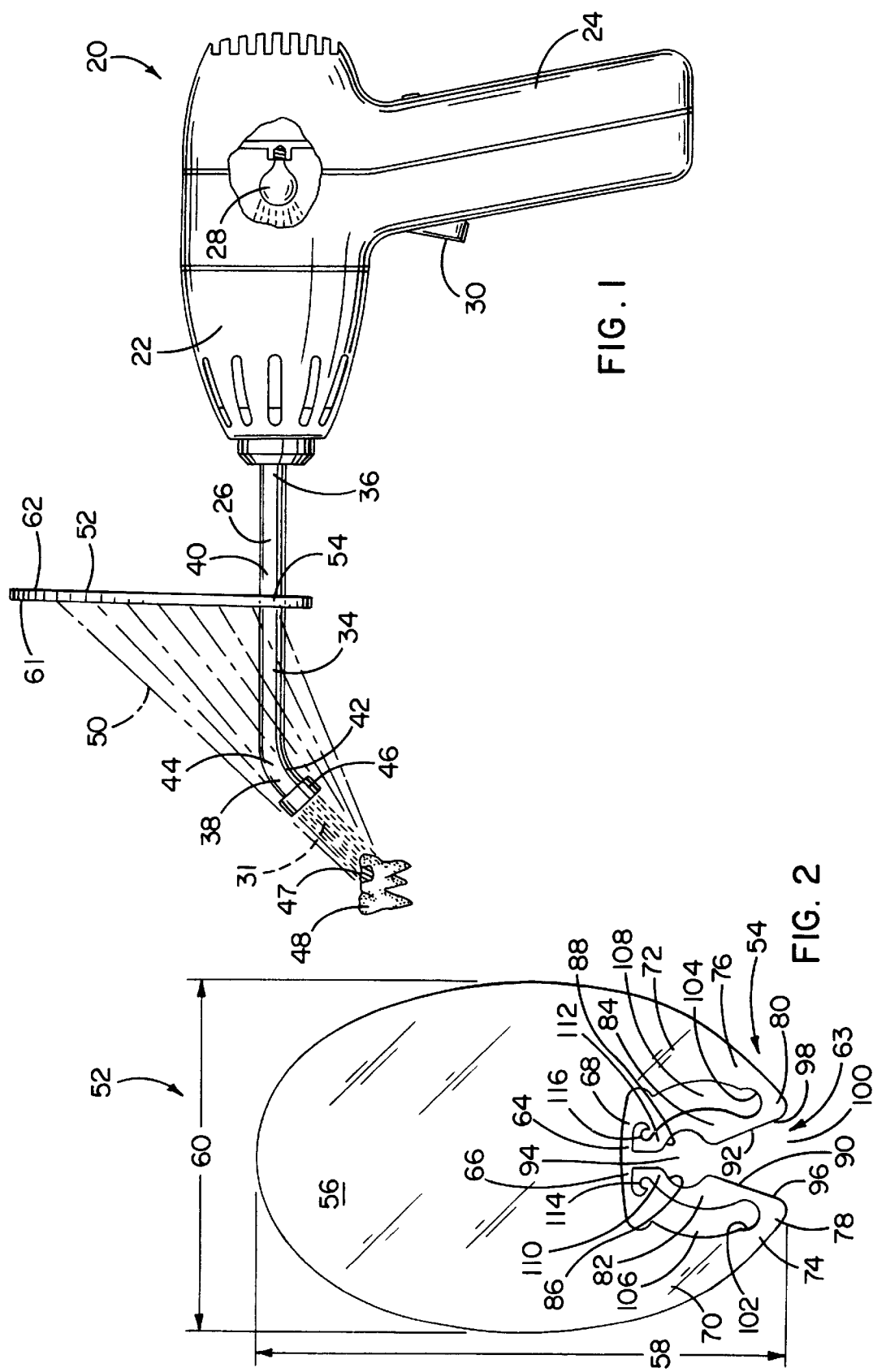

SNAP-ON LIGHT SHIELD FOR A DENTAL COMPOSITE LIGHT CURING GUN

FIELD OF THE INVENTION

The invention relates generally relates to dental tools and, more particularly, the invention relates to tools using light to cure dental composites.

BACKGROUND OF THE INVENTION

Dental restoration procedures often require various composites to be filled into a tooth cavity or area being repaired, and subsequently cured. With certain restoration procedures, the filling and curing cycle may be repeated multiple times. The curing process is often performed using a curing tool, which emits light from a source, such as a bulb, and through a bundle of optic fibers, to thus result in a focused light output. The light output is directed at the composite and the composite is quickly cured, a process also referred to as polymerization.

To facilitate the curing process, the fiber optic bundle is often provided within a probe or light guide extending from the curing tool or gun. The probe often extends linearly from the gun with an angular can't toward a distal end to enable the dentist or dental assistant to more easily access the particular tooth being repaired.

When the light is imparted against the dental composite and tooth surface, a certain component of the light is reflected back toward the dental tool, and thus the operator. Such light can be annoying or create a distracting glare for the operator, and more problematically can be a health hazard to the operator. Many light curing guns therefore include a shield positioned to block all or some of the reflective light. Since the field of vision of the operator cannot be impaired, such shields are often transparent, but tinted to absorb certain wavelengths of light. Typically, the shield is amber or orange tinted to absorb blue light reflected from the tooth surface, while allowing other wavelengths of the reflected light to pass through the shield.

Prior art protective shields are often secured with an elastomeric grommet disposable about the probe of the curing gun. The grommet typically has a central aperture with an inner diameter slightly smaller than the outer diameter of the probe. When the grommet and shield are attached to the probe, frictional interference between the grommet and probe secures the shield in place.

However, such prior art shields have proven to be difficult to remove, difficult to sterilize, and somewhat prone to premature attachment failure. More specifically, since the grommet includes an aperture, it must be attached and removed by sliding the grommet over the tip of the probe and linearly along the length of the probe. Not only is the frictional interference significant, but the tip of the probe is often provided with a protective rim of increased diameter which the grommet must overcome during attachment and detachment. Once removed, the plastic shield can be cold-sterilized with a suitable chemical, but the elastomeric grommet, typically made of rubber, cannot be sterilized. Moreover, the elastic properties of the rubber are temporary and can result in brittleness or breakage in the grommet, or in sufficient loss in elasticity to prevent adherence between the grommet and probe, thus resulting in an ineffective shield.

SUMMARY OF THE INVENTION

In accordance with one aspect of the invention, a light shield suitable for temporary attachment to a probe of a dental composite light curing gun is provided and may match a body of selectively transmissive material, first and second legs extending from the body, and a probe-engaging recess formed by cooperation of inner sides of the first and second legs. At least one of the first and second legs may be elastically deformed relative to the body.

In accordance with another aspect of the invention, a light shield is provided which may include a planar body of selectively transmissive material, and a mechanism for frictionally attaching the planar body to a substantially cylindrical surface. The planar body and mechanism may be manufactured from a unitary piece of material.

In accordance with another aspect of the invention, a light shield for a dental composite light curing gun having a fiber optic probe is provided which may include a planar body of selectively transmissive material, a recessed bay extending into the planar body, first and second legs extending into the recessed bay, and a probe resting notch defined by the first and second legs. Symmetrical portions of the planar body may be disposed on both sides of the recessed bay, with the first and second legs being adapted to elastically deform relative to the planar body at first and second hinge points. The first and second legs define a receiving space for the fiber optic probe leading to the probe resting notch.

These and other aspects and features of the invention may become more apparent from the following detailed description when taken in conjunction with the accompanying drawings.

BRIEF DESCRIPTION OF THE DRAWINGS

FIG. 1 is a side view of a curing gun employing a protective shield constructed in accordance with the invention;

FIG. 2 is a plan view of the protective shield unattached from the curing gun;

Figure 3:
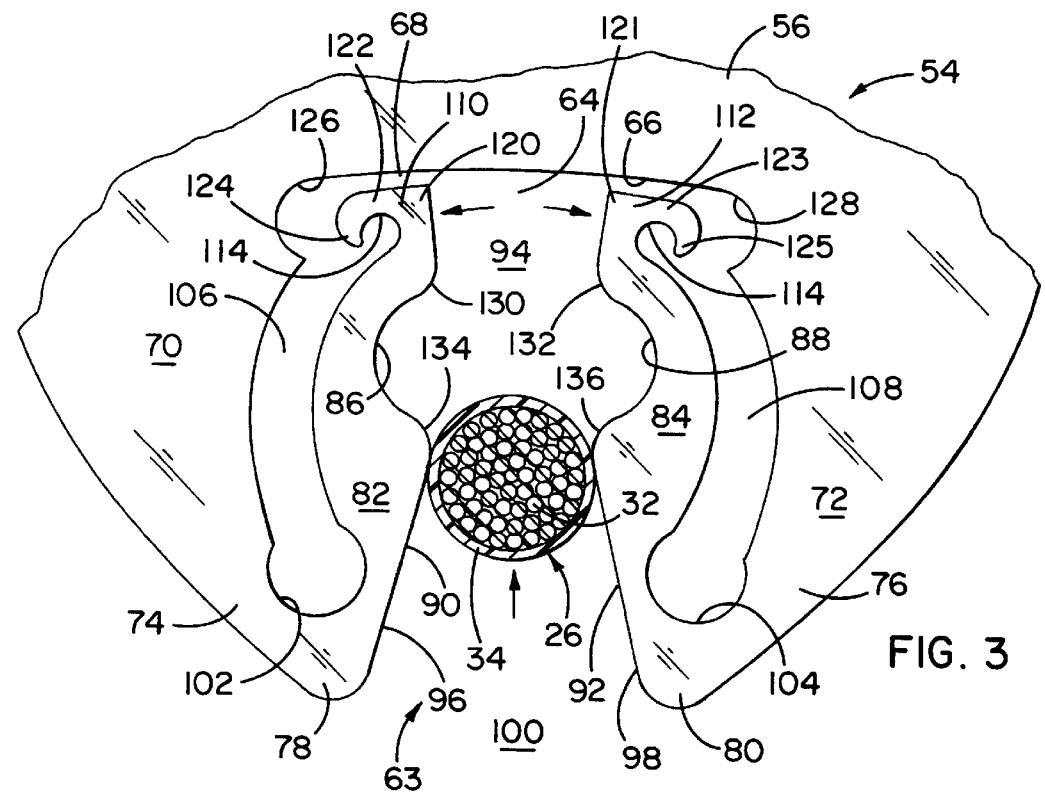
FIG. 3 is an enlarged fragmentary view of a connection end of the protective shield in the process of being attached to a probe of the curing gun, with the probe being depicted in cross-section.

While the invention is susceptible to various modifications and alternative constructions, certain illustrative embodiments thereof have been shown in the drawings and will be described below in detail. However, there is no intention to limit the invention to the specific forms disclosed, but on the contrary, the intention is to cover all modifications, alternative constructions, and equivalents falling within the spirit and scope of the invention as defined by the appended claims.

DETAILED DESCRIPTION OF THE PREFERRED EMBODIMENT

Referring now to the drawings, and with specific reference to FIG. 1, a dental composite curing gun according to the invention is generally depicted by reference numeral 20. As shown therein, the curing gun 20 may include a barrel 22, a grip 24, and a probe 26. The barrel 26 may house a light source or bulb 28, such as a tungsten halogen lamp, adapted to emit light when an electrical circuit thereto is closed by a trigger 30. The curing gun 20 is connected to a power source (not shown), typically AC power, although battery power is possible. The aforementioned elements of the gun 20 may vary from tool to tool, and simply serve as background environment for the invention, specifically the probe 26. Moreover, while the invention is depicted and described with reference to a dental curing gun, the protective shield of the invention can be employed with many other tools, medical and otherwise, wherein reflective light is to be shielded.

When the trigger 30 is actuated, light 31 is emitted by the bulb 28 and directed through the probe 26. The probe 26 typically includes a plurality of fiber optic fibers 32 (FIGS. 3 and 4) wrapped in a protective sheath or conduit 34. The conduit 34 may be manufactured from many materials, including fused glass. As shown, the conduit 34 may include a connection end 36, and a discharge end 38. The connection end 36 is typically provided with an attachment mechanism (not shown), to allow the probe 26 to be readily attached and detached from the gun 20, for purposes such as replacement or sterilization, such as through the use of an autoclave. A linear section 40 extends from the connection end 36 and merges into a canted section 42 proximate the discharge end 38. A nexus 44 defines the merger between the linear section 40 and the canted section 42. A protective rim 46 may be provided at the discharge end 38 to protect the end faces of the optic fibers 32. The rim 46 may be adhered to the probe 26 with a suitable adhesive, such as an epoxy adhesive.

As described above, the light 31 emitted by the gun 20 is used to cure a dental composite 47 deposited into a tooth 48. A portion of the emitted light 31 is reflected off of a surface of the tooth 48 as indicated by reference numeral 50. The reflected light 50 is sufficiently intense so as to pose a health hazard, particularly visually, to the dentist or dental assistant using the gun 20. At the very least, the reflected light 50 serves as an annoyance, and may create a glare interfering with the ability of the operator to accurately view the tooth 48 being restored.

A shield 52 may therefore be attached to the probe 26. The shield 52 is of sufficient dimension, and is positioned relative to the probe 26, so as to block or reflect the reflected light 50 before reaching the operator. Since the field of vision of the operator is of utmost importance, the shield 52 is preferably not opaque, but rather of a tinted nature to absorb certain wavelengths of the reflected light 50. For example, the shield 52 may be transparent with an amber- or orange-colored tint to absorb the blue light component of the reflected light 50. A suitable material from which the shield may be manufactured is polycarbonate plastic, such as that marketed by General Electric, under the trademark LEXAN. In addition, the shield 52 is preferably, although not necessarily manufactured by injection molding.

Figure 4:
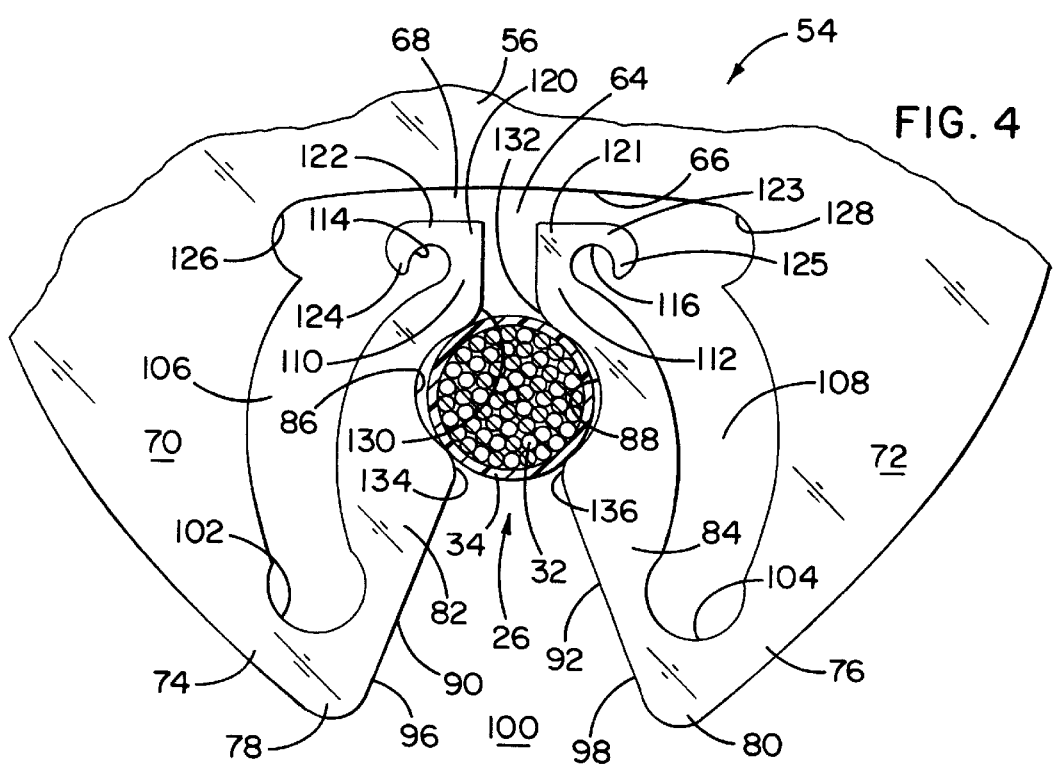
FIG. 4 is an enlarged fragmentary view of the connection end of the protective shield attached to a probe of the curing gun, with the probe being depicted in cross section.
Figure 5:
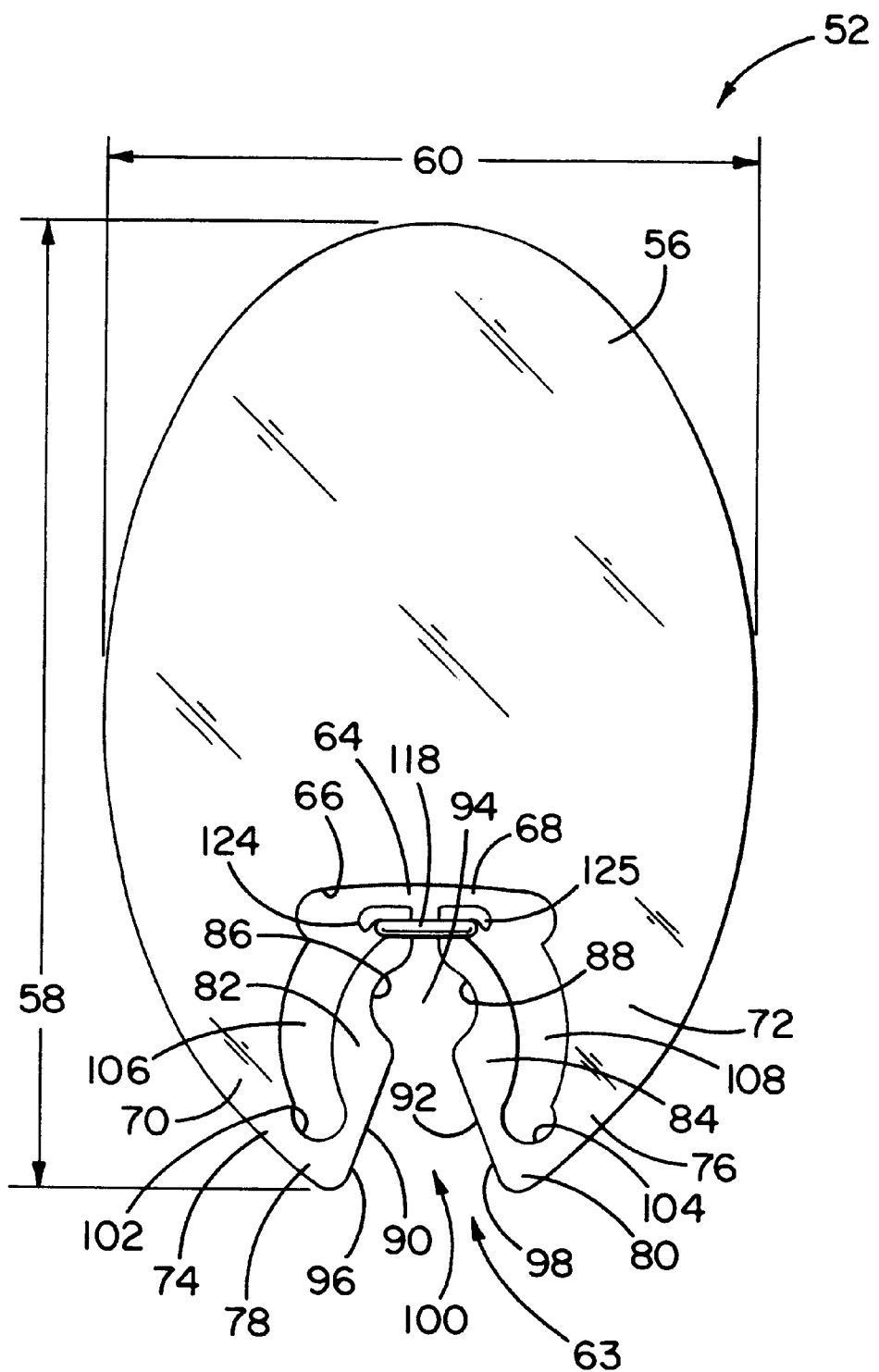
FIG. 5 is a plan view of a second embodiment of the protective shield including an elastomeric o-ring.

Turning now to FIGS. 2–4, the shield 52 and a snap-on connection mechanism 54 are shown in detail. As depicted, the shield 52 may include a light absorbing body 56. The body 56 may be planar across its length 58 and its width 60 and be polished on both a first side 61 and a second side 62 (FIG. 1) to serve as an optically and selectively transparent surface regardless of the side 61, 62 facing the tooth 48. Also, while the body 52 is depicted as having an oval shape, other shapes adapted for blocking the reflected light 50 are possible and within the scope of the invention. However, it is preferable that with all shapes employed, symmetrical portions of the main body be disposed laterally from the connection mechanism 54. Such a design balances the shield 52 and avoids any rotational moments which might tend to nonvertically orient the shield when attached to the probe 26.

Within a bottom end 63 of the body 56, it will be noted that a bay 64 is recessed therein. The bay 64 is defined by a ledge 66 at a closed end 68, and first and second arms 70 and 72 disposed laterally relative to the ledge 66. The first and second arms 70 and 72 include pivot ends 74 and 76, respectively, which merge into hinge sections 78, 80. The hinge sections 78, 80 in turn merge into clamping legs 82, 84, respectively. Given the elastic properties of the polycarbonate plastic from which the shield 52 is preferably manufactured, the legs 82, 84 are able to elastically deform laterally inward or outward relative to the arms 70, 72. Again, other materials having sufficient elastic properties are possible. It is also possible that the arms 70, 72 themselves be shaped and dimensioned to laterally deform for snapping the shield 52 onto the probe 26, without the use of the legs 82 and 84.

In order to secure the shield 52 to the probe 26, each leg 78, 80 may include an arcuate notch 86, 88. More specifically, inner sides 90, 92 of the legs 82, 84 may be contoured to include the arcuate notches 86, 88, which are positioned along the length 58 of the shield 52 so as to complementarily form a probe reception area 94. As shown in FIG. 3, it is within the probe reception area 94, that the probe 26 resides when the shield 52 is attached thereto.

As also shown in FIGS. 2–4, the shield 52 may include chamfers 96, 98 which facilitate attachment of the shield 52 to the probe 26 by guiding and directing the probe 26 first into a receiving gap 100 provided between the legs 82, 84 and eventually to the reception area 94 after the legs 82, 84 elastically deform outwardly.

Proximate chamfers 96, 98, and hinges 78, 80, semi-circular walls 102, 104 are provided. By employing the semi-circular walls 102, 104, as opposed to angular joints, the mechanical stress at the hinges 78, 80, resulting from the deformation of the legs 82, 84 is distributed over a broader area of the shield 52. In so doing, the serviceable life of the hinges 78, 80 and thus the shield 52 is enhanced.

Adjacent the semi-circular walls 94 and 96, it will be noted that arcuate slots 106 and 108 are provided with shapes complementary to the legs 82 and 84. Therefore, as the legs 82 and 84 laterally deform outwardly when the shield 52 is attached to the probe 26, the legs 82 and 84 are able to move into the arcuate slots 106 and 108 to accommodate such motion.

Receiving notches 114 and 116 are provided at upper ends 110, 112 of the legs 82, 84. While not employed in the embodiment shown in FIGS. 1–4, FIG. 5 shows that the receiving notches 114 and 116 are adapted to receive an o-ring 118 if additional inward biasing force is necessary to attach the shield 52 to the probe 26. This may be necessary, for example, when a probe 26 with a slightly smaller diameter than specified is utilized. By way of background only, it is important to note that such probes 26 are typically provided in diameters of 8 mm or 11 mm and the shield 52 can be manufactured to accommodate either, or any other dimension. If the probe 26 is manufactured to a slightly different dimension or tolerance, the o-ring 118 can be utilized to account for such differences. The o-ring 118 may be field installed by the user when appropriate.

More specifically, as shown best in FIGS. 3 and 4, each receiving notch 114, 116 includes a base wall 120, 121 from which a wall 122, 123 laterally extends. Each wall 122, 123 ends in a curled hook 124, 125 used to engage the o-ring 118 when provided within the receiving notches 114 and 116. The arcuate slots 108 and 110 include recesses 126 and 128, respectively, to receive the curled hooks 124, 125 during deformation of the legs 82 and 34. The o-ring 118 is preferably manufactured from an elastomeric material such as silicone or rubber, although other materials can be utilized.

In operation, the shield 52 is adapted to be snapped on to a probe 26 of the curing tool 20. The receiving gap 100 of the shield 52 defined by chamfers 96 and 98 is first positioned over the conduit 34 of the probe 26. Sufficient force is then imparted to the shield 52 by the operator once the probe 26 engages the legs 82 and 84, such that the legs 82 and 84 deform laterally outwardly at hinges 78 and 80 to a degree sufficient to allow the probe 26 to enter the probe reception area 94 (FIG. 3). The legs 82 and 84 then return inwardly given their natural elastic properties such that the arcuate notches 86 and 88 of the inner sides 90 and 92 engage the conduit 34 of the probe 26, as shown in FIG. 4. Upper nibs 130 and 132 proximate the arcuate notches 86 and 88 retain the probe 26 within the probe reception area 94 until sufficient force is imparted against the shield 52 to pull the shield 52 away from the probe 26. In so doing, the legs 82 and 84 again deform outwardly to allow the probe 26 to move past the lower nibs 134 and 136 through the receiving gap 100, and thus away from the shield 52. The shield 52, once removed, can be completely sterilized in that it is manufactured from a unitary piece of plastic, preferably polycarbonate.

From the foregoing, it can therefore be seen that the invention provides an improved light shield for a curing gun which allows for easy attachment and detachment from the probe of the curing gun through the use of its snap-on attachment mechanism. This is in contrast to prior art devices using rubber grommets which can only be removed or attached through the application of significant force required to slide the grommet along the entire length of the probe and around enlarged diameter sections of the probe, such as a protective rim at the end of the probe. Moreover, once removed, the entire shield of the invention can be sterilized.

What is claimed is:

1. A light shield suitable for temporary attachment to a probe of a dental composite light curing gun, said light shield comprising:
    a body of selectively transmissive material;
    first and second legs each extending from the body, each of the first and second legs including an inner side adjacent the inner side of the other leg, at least one of the first and second legs being elastically deformable relative to the body; and
    a probe-engaging recess formed by cooperation of the inner sides of the first and second legs.

2. The light shield of claim 1 wherein the body and first and second legs are manufactured from a unitary piece of material.

3. The light shield of claim 2 wherein the body and first and second legs are manufactured from polycarbonate plastic.

4. The light shield of claim 1 wherein first and second legs are symmetrically positioned relative to the body.

5. A light shield suitable for temporary attachment to a probe of a dental composite light curing gun, said light shield comprising:
    a body of selectively transmissive material;
    first and second legs each extending from the body, each of the first and second legs including an inner side adjacent the inner side of the other leg, at least one of the first and second legs being elastically deformable relative to the body; and
    a probe-engaging recess formed by cooperation of the inner sides of the first and second legs;
    wherein the body includes an inwardly directed bay, the first and second legs extending from the body into the bay.

6. The light shield of claim 5 wherein the first and second legs are each spaced by the tube-engaging recess and flanked by leg clearance slots.

7. A light shield suitable for temporary attachment to a probe of a dental composite light curing gun, said light shield comprising:
    a body of selectively transmissive material;
    first and second legs each extending from the body, each of the first and second legs including an inner side adjacent the inner side of the other leg, at least one of the first and second legs being elastically deformable relative to the body; and
    a probe-engaging recess formed by cooperation of the inner sides of the first and second legs;
    an elastomeric o-ring secured between the first and second legs.

8. The light shield of claim 7 wherein the first and second legs each include receiving notches adapted to receive the elastomeric o-ring.

9. A light shield suitable for temporary attachment to a probe of a dental composite light curing gun, said light shield comprising:
    a body of selectively transmissive material;
    first and second legs each extending from the body, each of the first and second legs including an inner side adjacent the inner side of the other leg, at least one of the first and second legs being elastically deformable relative to the body; and
    a probe-engaging recess formed by cooperation of the inner sides of the first and second legs;
    wherein the first and second legs connect to the body at hinge points, the hinge points including curved sides to minimize mechanical stress directly at the hinge points.

10. A light shield suitable for temporary attachment to a probe of a dental composite light curing gun, said light shield comprising:
    a body of selectively transmissive material;
    first and second legs each extending from the body, each of the first and second legs including an inner side adjacent the inner side of the other leg, at least one of the first and second legs being elastically deformable relative to the body; and
    a probe-engaging recess formed by cooperation of the inner sides of the first and second legs;
    wherein the body and first and second legs lie in the same plane.

11. A light shield, comprising;
    a body of selectively transmissive material; and
    a mechanism for frictionally attaching and detaching the body to a substantially cylindrical surface in a direction non-parallel to a longitudinal axis of the cylindrical surface, the body and mechanism being manufactured from a unitary piece of material.

12. The light shield of claim 11 wherein the unitary body and mechanism are completely sterilizable.

13. The light shield of claim 11 wherein the body and the mechanism are manufactured from amber-tinted, transparent polycarbonate plastic.

14. The light shield of claim 11 wherein the light shield is manufactured from injection-molded polycarbonate plastic.

15. A light shield, comprising:
    a planar body of selectively transmissive material; and
    a mechanism for frictionally attaching the planar body to a substantially cylindrical surface;

wherein the planar body and mechanism are manufactured from a unitary piece of material, and wherein the mechanism includes first and second legs extending from the planar body separated by a receiving recess, at least one of the first and second legs being elastically deformable to enlarge the receiving recess and attaching the light shield to the substantially cylindrical surface.

16. The light shield of claim 15 wherein the planar body includes a bay, the first and second legs extending into the bay.

17. The light shield of claim 15 further including an elastomeric o-ring secured to the first and second legs and spanning the receiving recess.

18. A light shield for a dental composite light curing gun having a fiber optic probe comprising:

a planar body of selectively transmissive material;

a recessed bay extending into the planar body, symmetrical portions of the planar body being disposed on both sides of the recessed bay;

first and second legs extending into the recessed bay, the first and second legs being elastically deformable relative to the planar body at first and second hinge points, the first and second legs defining a receiving space for a fiber optic probe; and a probe resting notch defined by the first and second legs proximate the receiving space.

19. The light shield of claim 18 wherein the light shield is manufactured from a unitary piece of material.

20. The light shield of claim 18 further including an elastomeric o-ring secured between the first and second legs.

* * * * *